United States Patent [19]

Nishioka et al.

[11] Patent Number: 4,987,884
[45] Date of Patent: Jan. 29, 1991

[54] ELECTRONIC ENDOSCOPE

[75] Inventors: Kimihiko Nishioka, Hachiouji; Hisao Ogiu, Oume; Tatsuo Nagasaki, Musashino, all of Japan

[73] Assignee: Olympus Optical Co., Ltd., Tokyo, Japan

[21] Appl. No.: 352,627

[22] Filed: May 16, 1989

Related U.S. Application Data

[63] Continuation of Ser. No. 102,249, Sep. 28, 1987, abandoned, which is a continuation of Ser. No. 813,774, Dec. 27, 1985, abandoned.

[30] Foreign Application Priority Data

Dec. 28, 1984 [JP] Japan ............................ 59-198856

[51] Int. Cl.$^5$ .............................................. A61B 1/06
[52] U.S. Cl. ........................................................ 128/6
[58] Field of Search ........................... 128/4–8, 128/23, 665; 250/211 J, 494.1; 350/438; 358/44

[56] References Cited

U.S. PATENT DOCUMENTS

| 4,034,396 | 7/1977 | Nakamura et al. | 250/211 J |
| 4,074,306 | 2/1978 | Kakinuma et al. | 128/6 |
| 4,253,447 | 3/1981 | Moore et al. | 128/6 |
| 4,345,269 | 8/1982 | Takemura | 358/44 |
| 4,540,250 | 9/1985 | Seto | 350/438 |
| 4,562,831 | 1/1986 | Murakoshi et al. | 128/6 |
| 4,582,998 | 4/1986 | Gonser et al. | 250/494.1 |
| 4,602,281 | 7/1986 | Nagasaki et al. | 128/6 |
| 4,604,992 | 8/1986 | Sato | 128/6 |
| 4,759,347 | 7/1988 | Ando | 128/6 |

Primary Examiner—Max Hindenburg
Attorney, Agent, or Firm—Cushman, Darby & Cushman

[57] ABSTRACT

An electronic endoscope using a solid-state image pickup device has a filter arranged in the foreground of the solid-state image pickup device within the body of the endoscope for removing lights having wavelengths not related to observation in order to effectively eliminate those light components which are not required for the observation from among those lights incident to the solid-state image pickup device. As such a filter, either a lens component constituting the objective lens or an illuminating lens can be used.

6 Claims, 4 Drawing Sheets

ELECTRONIC ENDOSCOPE

This is a continuation of application Ser. No. 07/102,249, filed Sept. 28, 1987, which was abandoned upon the filing hereof and which was a continuation of application Ser. No. 06/813774 filed Dec. 27, 1985, now abandoned.

BACKGROUND OF THE INVENTION

(a) FIELD OF THE INVENTION

The present invention relates to an electronic endoscope which uses a solid-state image pickup device.

(b) DESCRIPTION OF THE PRIOR ART

A solid-state image pickup device, in general, is sensitive to infrared rays, so that it is necessary for an electronic endoscope which uses, a solid-state image pickup device to have an infrared ray removing filter incorporated in its optical system. In the past, there has been known an electronic endoscope having such a structure as shown in FIG. 1. That is, in FIG. 1, reference numeral 1 denotes the body of an electronic endoscope; 2 a light supply; 3 an infrared ray removing filter; 4 a collector lens; 5 a light guide made of a bundle of optical fibers and housed in the body 1; 6 an illuminating lens housed in the forward end portion of the body 1; 7 an objective lens housed in the distal end portion of the body 1; 8 a solid-state image pickup device such as CCD housed in the forward end portion of the body 1; 9 a control unit inputted with a signal delivered from the solid-state image pickup device 8; and 10 a TV monitor. According to the electronic endoscope having such an arrangement as mentioned above, the beam of light emitting from the light supply 2 is removed of its infrared ray component by the infrared ray removing filter 3 and thereafter the resulting beam of light passes through the light supply lens 4 and through the light guide 5 and illuminates an object S through the illuminating lens 6. The light reflected from the object S which is thus illuminated is focused, by the objective lens 7, on the solid-state image pickup device 8, and the focused image is displayed on the TV monitor 10 by the control unit 9. In such a case, the beam of light which is incident to the solid state image pickup device 8 has been removed of its infrared ray component by the infrared ray removing filter 3, so that an appropriate image of the object can be displayed on the TV monitor 10. In this arrangement of the endoscope, however, the infrared ray removing filter 3 is disposed in the path of an intensive light supply, and accordingly there has been the inconvenience that the filter would crack as it is subjected to the heat produced by the beam of light coming from the light supply. Also, in case an irradiation of, for example, a laser beam is performed by means of a YAG laser 12 with a laser probe 11 made of a single optical fiber and passed through a forceps channel formed in the body 1 of the electronic endoscope, the laser beam thus produced is an infrared beam of light having a wavelength of 1061 nm. Therefore, the solid-state image pickup device 8 senses this laser beam, and as a result the observation is disturbed.

SUMMARY OF THE INVENTION

In view of the above-mentioned inconveniences of the prior art, it is the primary object of the present invention to provide an electronic endoscope arranged so that those components of light such as infrared rays which are incident to the solid-state image pickup device but unnecessary for the observation are removed.

According to the present invention, this object is attained by arranging, in the foreground of the solid-state image pickup device, a filter for removing the components of light having such wavelengths as are not useful for the observation. This filter may be a constituent part of the objective lens which is disposed in front of the solid-state image pickup device.

This and other objects of the present invention will become more apparent during the course of the following detailed description and appended claims.

DETAILED DESCRIPTION OF THE PREFERRED EMBODIMENTS

Figure 1:
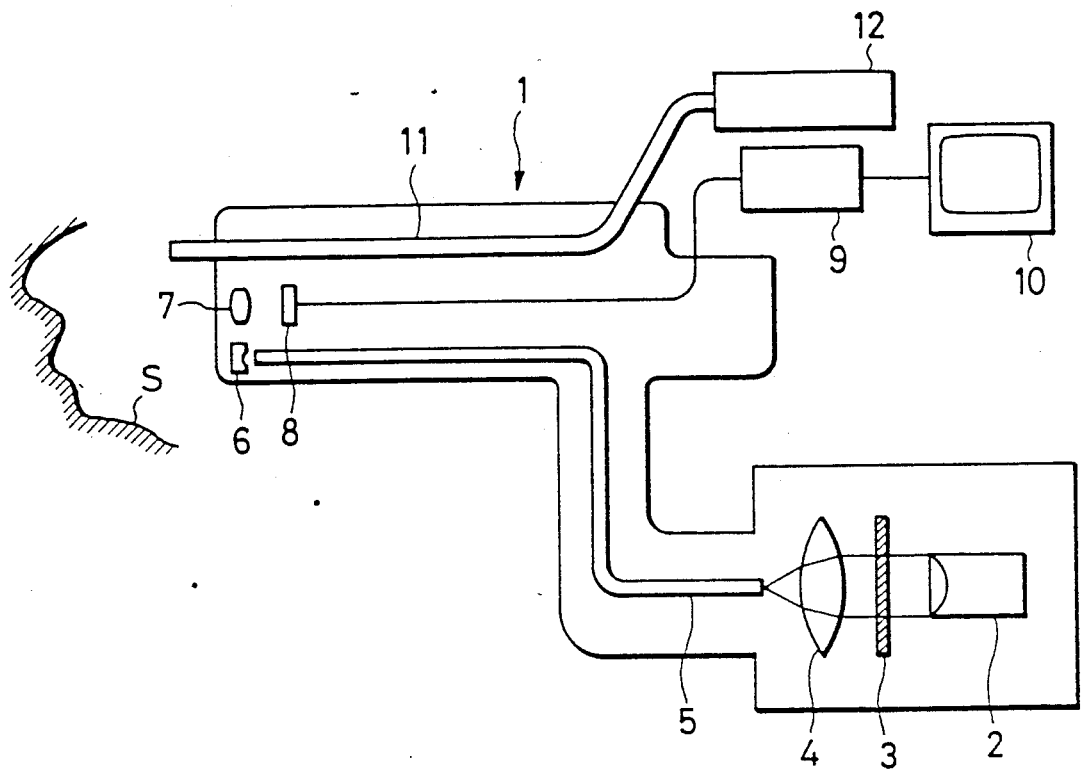
FIG. 1 is a diagrammatic representation showing the basic arrangement of the conventional electronic endoscope.

The present invention will hereunder be described in further detail with respect to the embodiments shown in the drawings. It should be understood that those constituent parts and members same as those shown in FIG. 1 are assigned with same reference numerals and symbol, and their detailed explanation is omitted. Numeral 13 represents an infrared ray removing filter which is disposed between the objective lens 7 and the solid-state image pickup device 8 in the distal end portion of the body 1 of the electronic endoscope.

Figure 3:
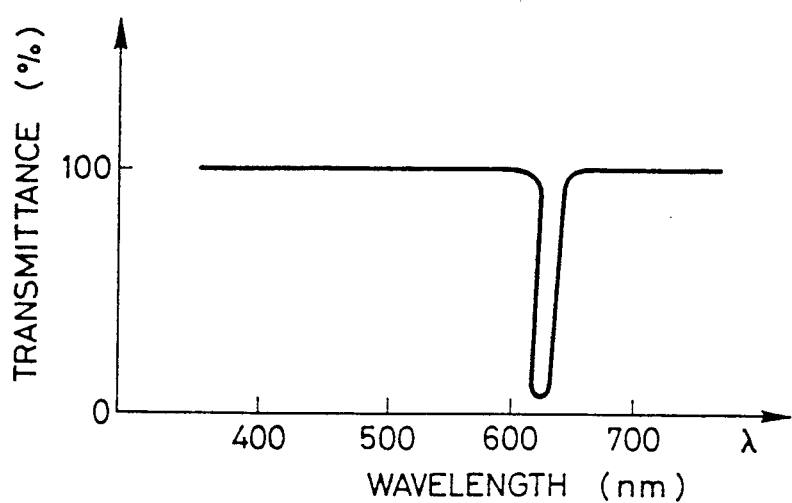
FIG. 3 is a chart showing the characteristics of the filter which is provided in the endoscope wherein a visible laser light is used.

The first embodiment of the present invention is arranged as stated above. Accordingly, the beam of light emitting from the light supply 2 illuminates the object S via the light guide 5 and the illuminating lens 6. The light reflected from the object S which is thus illuminated passes through the objective lens 7 to be focused, as an image, on the solid-state image pickup device 8 after being removed of its infrared ray component. Therefore, the image of the object S which is adequate for its observation can be displayed on the TV monitor 10 by the control unit 9. Also, even in case an irradiation of a laser beam is performed by a YAG laser 12, this laser beam is removed of its infrared ray component by the infrared ray removing filter 13, so that the observation is not hampered at all. Furthermore, because the infrared ray removing filter 13 is disposed in the foreground of the solid-state image pickup device 8, there never occurs the hazard that the filter cracks due to the intensive heat of the beam of light emitting from the light supply. It should be noted here that, in case a light other than the illuminating light beam, not to speak of the laser beam from the YAG laser, is used also, it is only necessary to use, in place of the infrared ray removing filter, a filter which removes such other light component. For example, in case a visible laser beam such as He-Ne laser beam having a wavelength of 632.8 nm is used, it is only necessary to employ a filter which does not transmit only such wavelength therethrough as shown in FIG. 3 in place of the infrared ray removing filter 13, and such an arrangement hardly affects the image which is observed.

Figure 4:
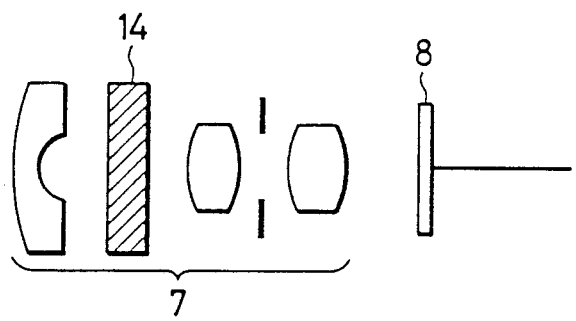
FIGS. 4 to 8 and 11 are illustrations showing other embodiments of the present invention.

FIG. 4 shows an essential portion of another embodiment according to the present invention. In this instant embodiment, an infrared ray removing filter 14 is disposed within the objective lens 7 which includes a stop, a negative lens and two positive lenses. According to this arrangement, there can be obtained a function similar to that obtained in the embodiment of FIG. 1, and moreover it is possible to compensate for the distortion as well as the chromatic aberration by such a filter 14.

Figure 2:
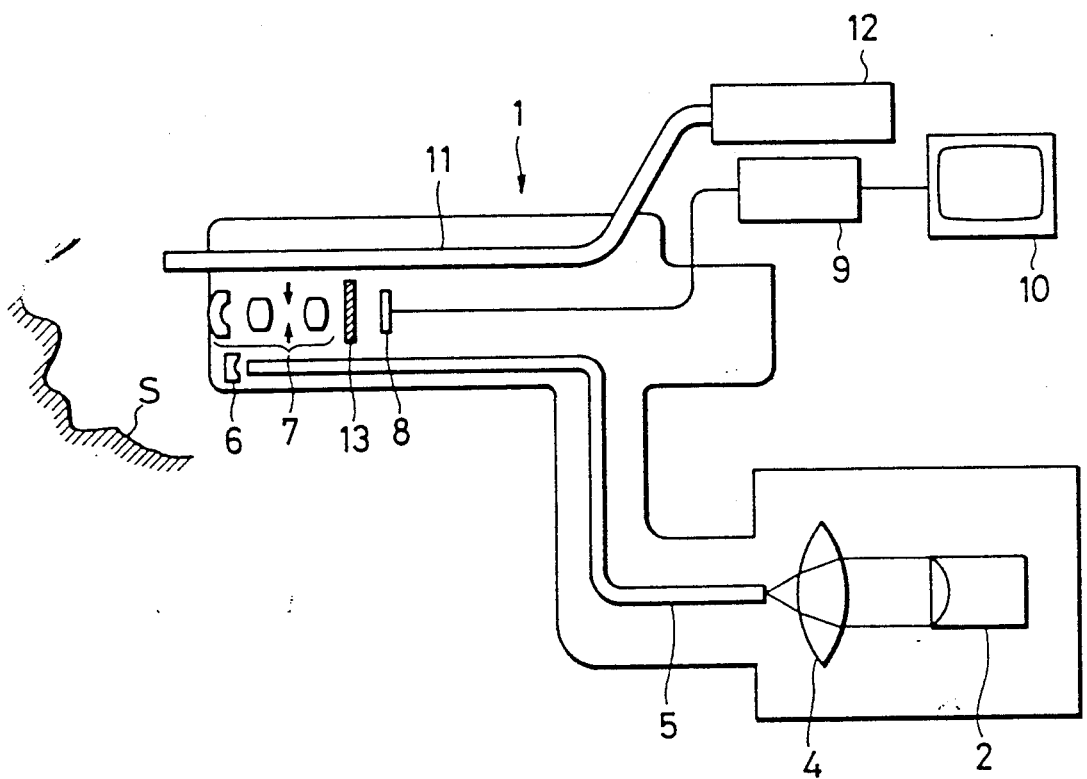
FIG. 2 is a diagrammatic representation showing the basic arrangement of an embodiment of the electronic endoscope according to the present invention.
Figure 5:
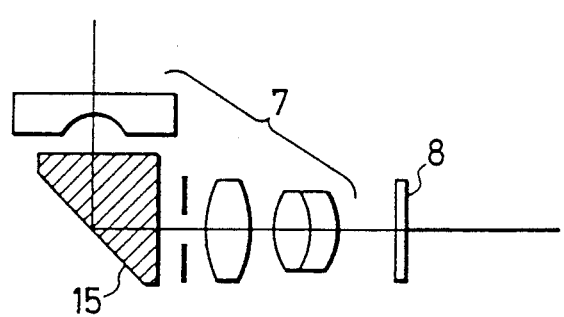

FIG. 5 is another embodiment wherein the present invention is applied to a flanked view type electronic endoscope. A prism 15 for bending the path of light is formed by an infrared ray removing glass within the objective lens 7, which also includes a stop, a negative lens, and two positive lenses. This prism functions as an infrared ray removing filter, and therefore a function same as that of the embodiment of FIG. 2 is obtained. This embodiment provides for a further advantage that the space for accomodating a filter becomes unnecessary.

Figure 6:
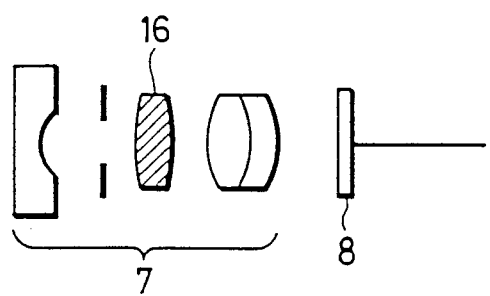

FIG. 6 shows another embodiment of the present invention. One 16 of the lens components constituting the objective lens 7 which contains a stop, a positive lens and a negative lens, is formed with an infrared ray removing glass. This lens component 16 functions to serve as an infrared ray removing filter, and thus a function similar to that of the embodiment of FIG. 1 is obtained. Moreover, the space for accomodating a filter is dispensed with.

Figure 7:
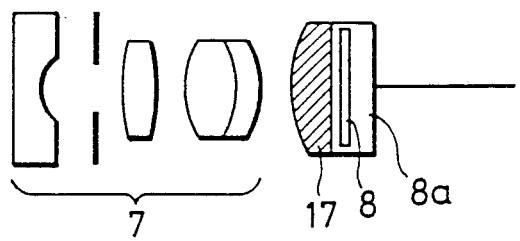

FIG. 7 shows still another embodiment of the present invention containing an objective lens unit 7 with components similar to that described above. Among the lens components constituting the objective lens 7, the rearmost lens component 17 is formed with an infrared ray removing glass and it is bonded to a package 8a of the solid-state image pickup device 8. This lens component 17 functions as an infrared ray removing filter, and in addition it serves for the protection of the solid-state image pickup device 8. Thus, a function similar to that of the embodiment of FIG. 6 is obtained, and furthermore this arrangement eliminates the need for the provision of a protecting member of the solid-state image pickup device 8. In this embodiment, the lens component 17 may be bonded directly to the surface of the solid-state image pickup device 8.

Figure 8:
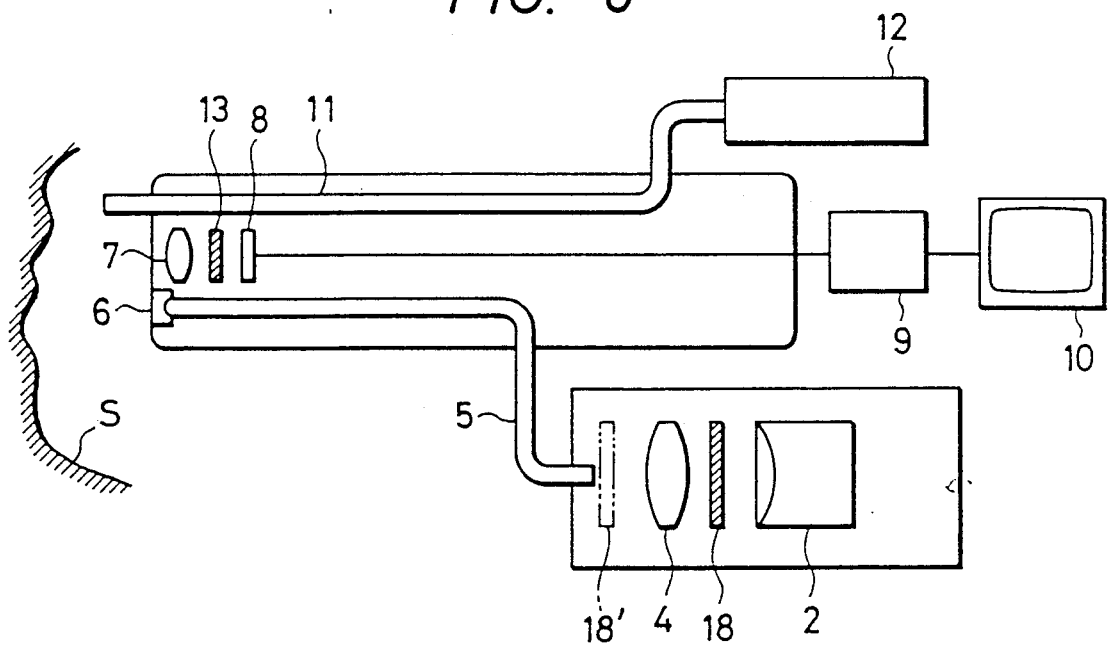
Figure 9:
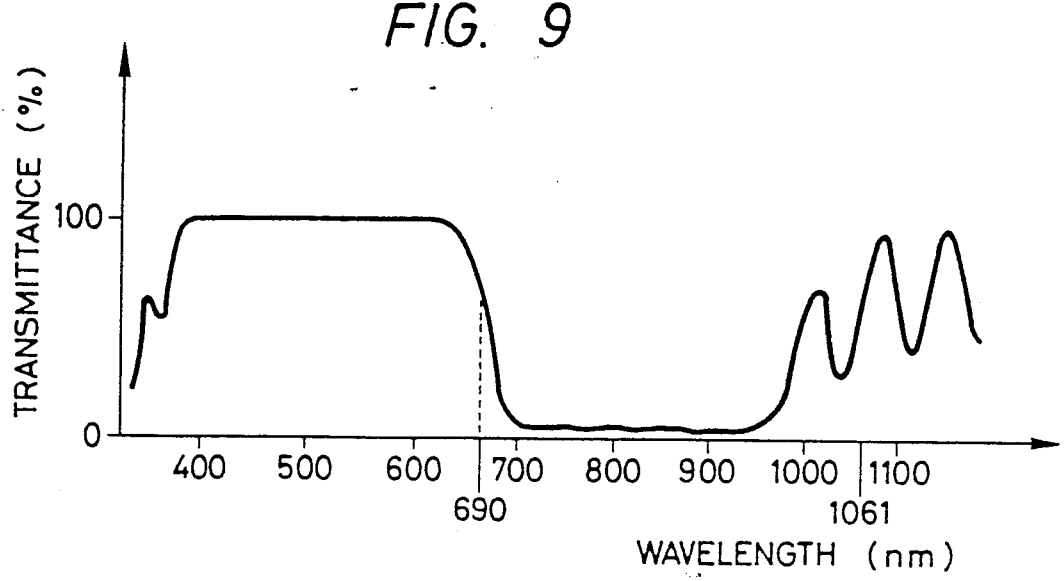
FIGS. 9 and 10 are charts showing the characteristics of the infrared ray removing filter which is used in the embodiment of FIG. 8.
Figure 10:
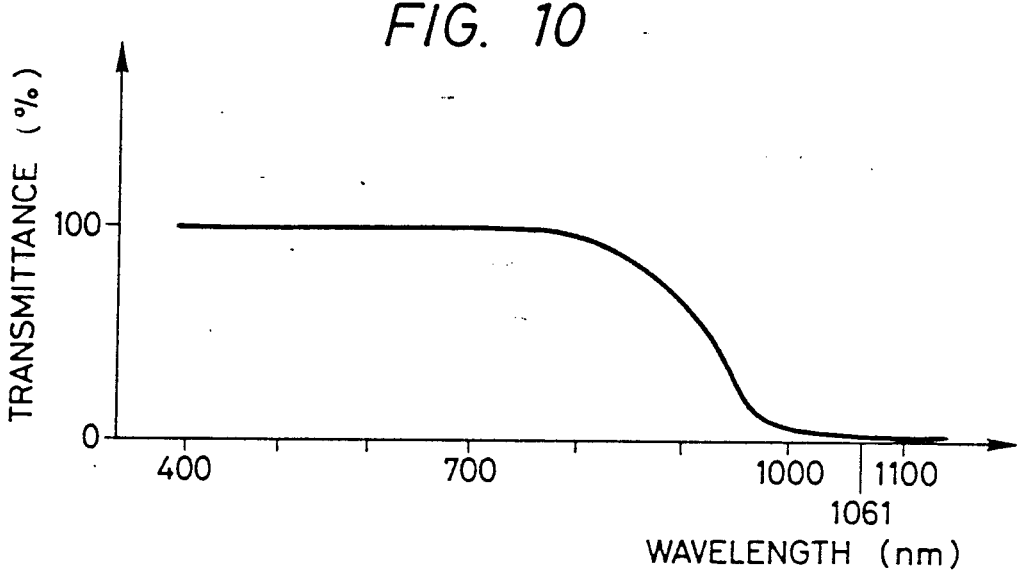

FIG. 8 shows an embodiment wherein an infrared ray removing filter 18 is provided also in front of the light supply 2 in the embodiment of FIG. 1. The filter 18 employed in this instant embodiment may be of any type so long as it removes a light having a wavelength in the range of 690 to 950 nm as shown exemplarily in FIG. 9. Also, the other filter 13 may be of any type as shown by way of example in FIG. 10 provided that it is capable of removing a light having a wavelength in the range of 950 to 1100 nm. According to this arrangement, it will be noted that, by means of these two infrared ray removing filters 13 and 18, infrared rays having a wide range of wavelengths from 690 to 1100 nm can be eliminated, and moreover the filter 13, in this embodiment, may be a heat-absorbing filter so long as it possesses such characteristics as shown in FIG. 10, so that there is the advantage that its manufacturing cost is low and that it has a prolonged service life.

Figure 11:
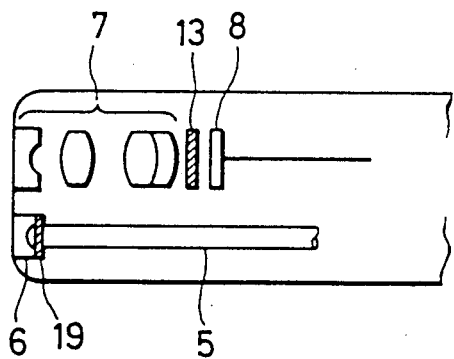

FIG. 11 is an embodiment which is of the arrangement that, in the embodiment of FIG. 8, in place of the filter 18, an infrared ray removing filter 19 is disposed between the light-emitting end of the light guide 5 and the illuminating lens 6. This instant embodiment provides for a function similar to that of the embodiment of FIG. 8. It should be noted here that such a function can be obtained also by arranging an infrared ray removing filter 18' at the light-incident end of the light guide 5 as shown by a chain line in FIG. 8, or by forming the illuminating lens 6 with an infrared ray removing glass. Moreover, this arrangement does not give rise to the development of cracks of the infrared ray removing filter by the heat of the light supply.

Description has been made of the instances wherein an infrared ray removing filter is provided. The arrangement does not need to be limited thereto. and it would be unnecessary to say that, by disposing a filter which removes lights having such wavelengths as irrelevant to the observation, it is possible to eliminate lights of arbitrary wavelengths also other than laser beams, visible lights and like beams of light rays. Furthermore, by replacing the infrared ray removing filter with either a color balance compensating filter or a compensation filter for color temperature, it is also possible to improve color reproduceability of the endoscope.

It should be understood here that, as the infrared ray removing filter, it is possible to use such one prepared by vapor-deposition of an infrared ray absorbing film onto a glass member such as glass plate, prism, lens and so forth, or such one which is produced by vapor-deposition, onto a glass member, of an interference film which reflects infrared rays. Also, if a heat ray absorbing glass is used as the glass member and if such a film as mentioned above is formed thereon, the resulting filter is desirable because it can exert the effect of eliminating infrared ray components in double manner.

What is claimed is:

1. An electronic endoscope comprising:
   illuminating means for radiating light toward an object, said illuminating means comprising:
   a light source for generating said light,
   at least one infrared ray removing filter means having a first spectral transmittance for filtering light having a wavelength of 690 to 950 nm, and
   means for guiding said filtered light toward said object; and
   image pickup means for imaging light reflected from said object, said image pickup means comprising:
   objective lens unit means for focussing said light, and
   heat ray absorbing filter means having a second spectral transmittance for filtering light having a wavelength of 950 to 1100 nm so that, as a whole, said infrared ray removing filter means and said heat ray absorbing filter means remove infrared rays and YAG laser beams ranging in wavelength from 690 to 1100 nm.

2. An electronic endoscope according to claim 1 wherein said objective lens unit means comprises a stop, a negative lens on an object side of said stop, and at least two positive lenses on an image side of said stop.

3. An electronic endoscope according to claim 2 wherein said heatray absorbing filter means is a prism disposed in said objective lens unit means between said negative lens and said two positive lenses.

4. An electronic endoscope according to claim 2, wherein said heat ray absorbing filter means is formed as one of said positive and negative lenses.

5. An electronic endoscope according to claim 2, wherein said image pickup means comprises a solid-state image pickup device, and said heat ray absorbing filter and said image pickup device are arranged in mutually spaced relation.

6. An electronic endoscope according to claim 1, wherein said image pickup means comprises a solid-state image pickup device, and said heat ray absorbing filter and said image pickup device are arranged in mutually spaced relation.

* * * * *